United States Patent [19]

Baum et al.

[11] Patent Number: 4,465,834

[45] Date of Patent: Aug. 14, 1984

[54] ANTICHOLINERGIC DRUGS

[75] Inventors: Burton M. Baum, Hopewell; Hugo Stange, Princeton, both of N.J.

[73] Assignee: FMC Corporation, Philadelphia, Pa.

[21] Appl. No.: 488,804

[22] Filed: Sep. 20, 1965

[51] Int. Cl.³ .................. C07D 451/02; C07D 451/04; C07D 451/06
[52] U.S. Cl. .................. 546/127; 424/265; 424/267; 424/274; 546/137; 546/242; 548/565
[58] Field of Search ............ 260/287, 294.3 C, 313.1, 260/326.3, 468, 473 A, 484, 486; 167/55 A; 424/256, 265, 267, 274, 298, 308; 546/127, 137, 242; 548/565

[56] References Cited

U.S. PATENT DOCUMENTS 3,091,570 5/1963 Beil .......................... 167/55 A X
3,094,463 6/1963 Beil .......................... 167/55 A X

OTHER PUBLICATIONS

Ing, Alkaloids, vol. 5, pp. 247–251 (1955).

*Primary Examiner*—Leland A. Sebastian
*Attorney, Agent, or Firm*—Robert D. Jackson; Milton Zucker

[57] ABSTRACT

A class of anticholinergic drugs having the formula

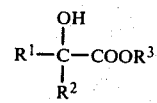

in which $R^1$ is a carbocyclic or branched aliphatic group of 3 to 8 carbon atoms, $R^2$ is a branched or linear aliphatic group containing 3 to 10 carbon atoms with 1 to 2 olefinic or acetylenic bonds and $R^3$ is an alkyl or cyclic group of 4 to 12 carbon atoms containing a tertiary amino nitrogen, are described.

4 Claims, No Drawings

ANTICHOLINERGIC DRUGS

This invention relates to novel chemicals which are useful as anticholinergic drugs possessing unique advantages in their improved time of action.

It is known that esters of basic nitrogen-containing alcohols and substituted glycolic acids, such as benzilic acid and α-cyclopentyl-α-phenyl-glycolic acid, have marked anticholinergic activity and various of these materials have been reported to have useful cycloplegic or mydriatic action and to be of value in treating mental illnesses, certain neurological diseases and disorders of the gastrointestinal tract. However, known drugs often have unsuitable time-action courses. They typically react only after a considerable onset period, and the effects generally linger on for a fair number of hours. There has been a need for anticholinergic drugs which will act in shorter times, but especially for such drugs whose effects wear off rapidly, such as in the cycloplegic diagnostic examination of the eyes.

We have discovered a new class of substituted glycolates which possess potent anticholinergic activity, excellent mydriatic properties, generally characterized by short onset times and by short durations of action, and high therapeutic indices.

These products are esters of substituted glycolic acids (including their acid addition and quaternary salts) having the general formula $R^1,R^2C(OH)COOR^3$, in which $R^1$ is a carbocyclic or branched aliphatic group of 3 to 8 carbon atoms, such as phenyl, cyclohexyl, cyclopentyl, cyclopropyl, cycloheptyl and isopropyl; $R^2$ is a branched or linear aliphatic group containing 3 to 10 carbon atoms with 1 or 2 acetylenic or olefinic bonds, such as $CH_3(CH_2)_nC\equiv C-$ (where n is 0 to 7), $(CH_3)_2CHC\equiv C-$, $(CH_3)_3C-C\equiv C-$, $CH_3(CH_2)_nCH=CH-$ (where n is 0 to 7),

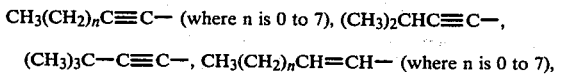

$HC\equiv CCH_2-$, $(C_2H_5)_2CHC\equiv C-$, or is a phenylethynyl, a styryl, or an ethynyl group; and $R^3$ is an alkyl or cyclic group of 4 to 12 carbon atoms containing a tertiary amino nitrogen. The most potent compounds are those in which the tertiary amino nitrogen of $R^3$ is part of a ring system, such as 1-methyl-3-piperidyl (referred to in the Tables as 3P), 1-methyl-4-piperidyl (4P), 3-quinuclidyl (3Q), 1-methyl-3-pyrrolidinyl (3PY), 1-methyl-3-piperidyl-methyl (3P—$CH_2$—), 1-methyl-4-piperidyl-methyl (4P—$CH_2$—), 3α-tropanyl (3αT), and 2-methyl-3-quinuclidyl (2MQ).

The compounds of this invention may be used as either the free base or the acid-addition and quaternary ammonium salt forms thereof. The anions of the salts of this invention should be non-toxic and may include, for example, chloride, bromide, sulfate, tartrate, p-toluenesulfonate and the like.

Although many esters of substituted glycolic acids and alcohols containing a tertiary amino group are well known, none having a linear or branched chain containing acetylenic and/or olefinic linkages in the glycolic acid moiety have been described. It is this type of unsaturation which is believed to be responsible for the improved properties of the products of this invention.

These products may be prepared by transesterifying simple lower alkyl esters of these substituted glycolic acids with the proper tertiary nitrogen-containing alcohol using known techniques in accordance with the following equation:

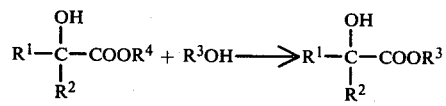

where $R^4$=lower alkyl. An inert solvent such as benzene, normal heptane, toluene or other solvent which will azeotrope the lower alkanol is employed, and alkali metals or alkali metal alkoxides are satisfactory catalysts.

The salts of the compounds of this invention are prepared by conventional methods generally involving the reaction of the free base with the appropriate inorganic or organic acid, or alkylating agent, in a suitable, inert medium.

The simple lower alkyl ester intermediates are prepared by reaction of a suitable organometallic reagent containing the unsaturated $R^2$ group with the corresponding substituted lower alkyl esters of glyoxylic acids.

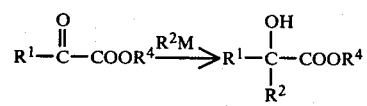

Alternatively, it may be desirable, under circumstances where the unsaturated substituted glycolates tar up on transesterification, to prepare the tertiary amino esters of the glyoxylate and then to react these tertiary amino-containing glyoxylates with a suitable organometallic reagent.

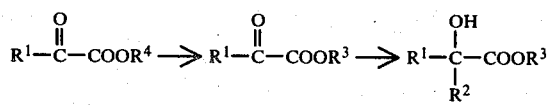

The simple lower alkyl glyoxylates may be prepared by the method of Bouveault and Locquin, Compt. rend., 135, 179 (1902) as modified by R. Fischer and T. Weiland, Chem. Ber., 93, 1387 (1960) or of M. Igarashi and H. Midorikawa, J. Org. Chem., 28, 3088 (1963).

The final products, which contain olefinic rather than acetylenic linkages, may be prepared analogously using olefinic organometallic reagents or by the partial hydrogenation of the lower alkyl acetylenic glycolate prior to the final transesterification.

The examples given herewith are given by way of illustration and not by way of limitation of the invention.

The following example represents a novel substituted glyoxylate.

EXAMPLE 1

Preparation of n-butyl Cyclopropylglyoxylate

Cyclopropylmagnesium bromide was prepared from 48 g. of cyclopropyl bromide and 11 g. of magnesium in the customary manner. The Grignard reagent was then treated with 162 g. di-(n-butyl) oxalate and the reaction mixture decomposed with an aqueous ammonium chloride solution. The organic material was separated and stripped of volatile components in vacuo. The residue was subsequently distilled to yield 19.3 g. (27%) of n-butyl cyclopropylglyoxylate, b.p. 108° (13 mm.).

Anal. Calcd. for $C_8H_{14}O_3$: C, 63.51; H, 8.29. Found: C, 63.74; H, 8.17.

The structure of this ester was confirmed by n.m.r. analysis.

The following examples are of the preparation of the intermediate lower alkyl glycolate from the glyoxylate.

EXAMPLE 2

Preparation of Ethyl α-Phenyl-α-phenylethynylglycolate

A solution of phenylacetylene (11.2 g., 0.1 mole) in 25 ml. of anhydrous ether was added over a 45 minute period to a suspension of ethylmagnesium bromide (0.1 mole) prepared from magnesium (2.4 g., 0.1 g. atom) and ethyl bromide (10.9 g., 0.1 mole) in 100 ml. of ether. The mixture was stirred overnight. The resultant phenylethynylmagnesium bromide suspension was subsequently added dropwise through a stop-cock at the base of the flask to a solution of ethyl phenylglyoxylate (17.8 g., 0.1 mole) in 100 ml. of dry ether at 0°–5° over a two hour period. The cooling bath was removed and the mixture stirred for five hours. The reaction mixture was kept overnight, then poured on a slurry of ice and concentrated hydrochloric acid and extracted with ether. The ether extracts were dried and the solvent distilled in vacuo. The resultant oil was distilled to give 14.5 g. (52%) of product, b.p. 170°–82° (0.25 mm.). An analytical sample distilled at 156°–58° (0.08 mm.).

Anal. Calcd. for $C_{18}H_{16}O_3$: C, 77.13; H, 5.75. Found: C, 77.31; H, 5.82.

N.m.r. and infrared analyses confirmed the structure.

In another experiment on a larger scale the reaction mixture was refluxed only two hours after the addition of phenylacetylene (33.6 g., 0.3 mole) until no more methane was evolved, when conversion to phenylethynylmagnesium bromide was assumed to be complete. The addition of the Grignard reagent to the ester was carried out immediately thereafter. The yield was 52.8 g. (63%).

EXAMPLE 3

Preparation of Methyl α-Phenyl-α-(1-propynyl)glycolate

1-Propynylmagnesium bromide (0.2 mole) was made from magnesium (4.8 g., 0.2 g. atom) ethyl bromide (21.8 g., 0.2 mole) and excess propyne gas in 400 ml. of THF. The Grignard reagent then was siphoned under nitrogen into an addition funnel and added dropwise over a 40 minute period to a cooled solution of methyl phenylglyoxylate (32.8 g., 0.2 mole) in 200 ml. of THF. A slight temperature rise took place. The reaction mixture was stirred for 24 hours, and then poured onto a slurry of ice and 25 ml. conc. HCl. Ether was added, and the layers were separated. Several more ether extracts were made and the organic extracts combined and dried. The volatile components were stripped subsequently in vacuo and the residue distilled to yield 13.1 g. (32%) of the product, b.p. 109°–12° (0.2 mm.). The oil solidified on standing and melted at 64°–65° after recrystallization from 20°–40° petroleum ether.

Anal. Calcd. for $C_{12}H_{12}O_3$: C, 70.57; H, 5.92. Found: C, 70.73; H, 5.81.

The n.m.r. spectrum of this compound was in agreement with the assigned structure.

The preparation of other acetylenic lower alkyl glycolates made similarly is summarized in Tables 1 and 2. The structures of these compounds were verified by n.m.r. spectroscopy.

TABLE 1

ACETYLENIC PHENYL-GLYCOLATE INTERMEDIATES
$R^1, R^2C(OH)COOR^4, R^1 = C_6H_5, R^4 = CH_3$

| | $R^2$ | Crude Yield, % | B.P., °C. (mm) | Empirical Formula | C Calcd. | C Found | H Calcd. | H Found |
|---|---|---|---|---|---|---|---|---|
| 1 | HC≡C— | 41 | 88–91(0.1) | $C_{11}H_{10}O_3$ | 69.47 | 69.27 | 5.30 | 5.50 |
| 2 | HC≡C—CH₂— | 32 | 110–111(1.2) | $C_{12}H_{12}O_3$ | 70.57 | 70.39 | 5.92 | 5.84 |
| 3 | CH₃CH₂C≡C— | 51 | 53–56* | $C_{13}H_{14}O_3$ | 71.54 | 71.25 | 6.46 | 6.58 |
| 4 | CH₃(CH₂)₂C≡C— | 34 | 111(.05) | $C_{14}H_{16}O_3$ | 72.40 | 72.21 | 6.94 | 6.98 |
| 5 | (CH₃)₂CHC≡C— | 67 | 105(.05) | $C_{14}H_{16}O_3$ | 72.40 | 72.24 | 6.94 | 7.18 |
| 6 | (CH₃)₃CC≡C— | 53 | 105–106(.04) | $C_{15}H_{18}O_3$ | 73.14 | 73.35 | 7.37 | 7.61 |
| 7 | CH₃(CH₂)₃C≡C— | 60 | 122(.07) | $C_{15}H_{18}O_3$ | 73.14 | 73.16 | 7.37 | 7.42 |
| 8 | CH₃(CH₂)₄C≡C— | 67 | 132(.07) | $C_{16}H_{20}O_3$ | 73.82 | 73.66 | 7.74 | 7.60 |
| 9 | CH₂=C(CH₃)C≡C— | 36 | 110–118(.003) | $C_{14}H_{14}O_3$ | 73.02 | 73.13 | 6.13 | 6.12 |

*M.P.

TABLE 2

ACETYLENIC ALKYL- AND CYCLOALKYL-GLYCOLATE INTERMEDIATES, $R^1R^2C(OH)COOR^4$

| | $R^1$ | $R^2$ | $R^4$ | Yield % | B.P. °C.(mm.) | Empirical Formula | C Calcd. | C Found | H Calcd. | H Found |
|---|---|---|---|---|---|---|---|---|---|---|
| 1. | Cyclopropyl | CH₃C≡C— | C₄H₉—n | 39 | 107–112(2.3) | $C_{12}H_{18}O_3$ | 68.54 | 68.28 | 8.63 | 8.57 |
| 2. | Cyclopentyl | HC≡C— | CH₃ | 50 | 78–80(1.5) | $C_{10}H_{14}O_3$ | 65.92 | 65.90 | 7.74 | 7.97 |
| 3. | Cyclopentyl | CH₃C≡C— | CH₃ | 27 | 107(2.5) | $C_{11}H_{16}O_3$ | 67.32 | 66.90 | 8.22 | 8.58 |
| 4. | Cyclopentyl | CH₃CH₂C≡C— | C₂H₅ | 59 | 100–109(0.9) | $C_{13}H_{20}O_3$ | 69.61 | 69.80 | 8.99 | 8.78 |
| 5. | Cyclopentyl | CH₂=C(CH₃)C≡C— | C₂H₅ | 71 | 81–88(.002) | $C_{14}H_{20}O_3$ | 71.16 | 71.32 | 8.53 | 8.69 |
| 6. | Cyclopentyl | (CH₃)₂CHC≡C— | C₂H₅ | 59 | 94–96(0.5) | $C_{14}H_{22}O_3$ | 70.56 | 70.43 | 9.31 | 9.13 |
| 7. | Isopropyl | CH₃C≡C— | C₂H₅ | 60 | 113–115(20) | $C_{10}H_{16}O_3$ | 65.15 | 65.33 | 8.75 | 8.90 |
| 8. | Cyclohexyl | CH₃C≡C— | C₂H₅ | 74 | 107(0.75) | $C_{13}H_{20}O_3$ | 69.61 | 69.46 | 8.99 | 9.07 |
| 9. | Cyclohexyl | CH₃CH₂C≡C— | C₂H₅ | 60 | 111–114(1.2) | $C_{14}H_{22}O_3$ | 70.56 | 70.35 | 9.31 | 9.19 |
| 10. | Cyclohexyl | CH₂=C(CH₃)C≡C— | C₂H₅ | 60 | 88–103(.003) | $C_{15}H_{22}O_3$ | 71.97 | 71.82 | 8.86 | 8.67 |

TABLE 2-continued

ACETYLENIC ALKYL- AND CYCLOALKYL-GLYCOLATE INTERMEDIATES, $R^1R^2C(OH)COOR^4$

| | | | Yield | B.P. | Empirical | Analysis | | | |
|---|---|---|---|---|---|---|---|---|---|
| | | | | | | C | | H | |
| $R^1$ | $R^2$ | $R^4$ | % | °C.(mm.) | Formula | Calcd. | Found | Calcd. | Found |
| 11. Cyclohexyl | $(CH_3)_2CHC\equiv C-$ | $C_2H_5$ | 58 | 90–100(0.5) | $C_{15}H_{24}O_3$ | 71.39 | 71.42 | 9.59 | 9.39 |

Typical of the methods used for preparing olefinic glycolates are the following preparations.

EXAMPLE 4

Preparation of Ethyl α-Phenyl-α-styrylglycolate

Ethyl α-phenyl-α-phenylethynylglycolate (5.6 g., 0.02 mole) in 50 ml. of absolute ethanol, 0.2 g. of palladium on barium sulfate and a drop of quinoline were placed in a Parr shaker under 40 psi of hydrogen at room temperature. The required amount of hydrogen was taken up in 13 minutes. The catalyst was filtered and the filtrate stripped of ethanol in vacuo to yield 5.7 g. (100%) of crude product. Both n.m.r. and infrared spectroscopy confirmed the structure. The material was distilled to yield 4.1 g. of liquid, b.p. 130°-43° (0.16 mm.). N.m.r. analysis of the distilled material indicated that about 5 mole % of the fully saturated derivative was present as an impurity.

EXAMPLE 5

Methyl α-Phenyl-α-(trans-1-propenyl)glycolate

Lithium ribbon (1.0% Na content) 6.9 g., 1.0 g. at.) was cut into strips (1.0 cm.=0.089 g.), degreased in hexane and cut into thin strips into ether (200 ml.) under helium. The reaction flask was equipped with dry-ice condenser and trans-propenyl chloride (25.5 g., 0.30 mole) was introduced dropwise during 60 minutes to the rapidly stirred suspension. The reaction was exothermic and was controlled by the addition of the halide. After addition the mixture was stirred for an additional 60 minutes. The trans-propenyllithium slurry was subsequently siphoned (in spurts during 30 minutes by He.pressure) into a stirred solution containing methyl phenylglyoxylate (55.0 g., 0.3 mole) in ether which was cooled to −78°. After 30 minutes of additional stirring, the reaction was warmed to −10° and poured onto 30 ml. of concentrated HCl and ca. 200 g. of ice. The ether layer was separated and the aqueous layer was further extracted with 3×50 ml. of ether. All ether layers were combined and dried over Drierite for 18 hours. After the solvent was stripped, the crude product weighting 58.1 g. (94%) was obtained which on distillation afforded 35 g. (57%) of pure material, b.p. 100° (0.05 mm.).

Anal. Calcd. for $C_{12}H_{14}O_3$: C, 69.88; H, 6.84. Found: C, 69.58; H, 6.77.

This sample was identified by n.m.r. and infrared spectroscopy.

Additional olefinic lower alkyl glycolates made similarly are listed in Table 3. Method H indicates that the olefinic glycolate was prepared via hydrogenation of the corresponding acetylenic lower alkyl glycolate. Method M indicates that the olefinic glycolate was prepared from the corresponding lower alkyl glyoxylate and a suitable olefinic organometallic reagent e.g. 2-propenylmagnesium bromide. The structures of these compounds were verified by n.m.r. spectroscopy.

TABLE 3

OLEFINIC ALKYL- AND CYCLOALKY-GLYCOLATE INTERMEDIATES, $R^1R^2C(OH)COOR^4$

| | | | | Crude Yield | B.P. | Empirical | Analysis | | | |
|---|---|---|---|---|---|---|---|---|---|---|
| | | | | | | | C | | H | |
| $R^1$ | $R^2$ | $R^4$ | Method | % | °C. (mm.) | Formula | Calcd. | Found | Calcd. | Found |
| 1. Isopropyl | $CH_3CH=CH-$ | $C_2H_5$ | H | 100 | 96–98(17) | $C_{10}H_{18}O_3$ | 64.49 | 64.71 | 9.74 | 9.90 |
| 2. Cyclopentyl | $CH_3CH=CH-$ | $C_2H_5$ | H | 100 | 62–64(.07) | $C_{12}H_{20}O_3$ | 67.89 | 67.94 | 9.50 | 9.21 |
| 3. Cyclopentyl | $CH_3CH_2CH=CH-$ | $C_2H_5$ | H | 100 | 70(.10) | $C_{13}H_{22}O_3$ | 68.99 | 69.25 | 9.80 | 9.63 |
| 4. Cyclopentyl | $(CH_3)2HCCH=CH-$ | $C_2H_5$ | H | 99 | 75–77(.03) | $C_{14}H_{24}O_3$ | 69.96 | 70.24 | 10.07 | 10.21 |
| 5. Phenyl | $CH_3CH=CH-$ | $CH_3$ | H | 100 | 65(.04) | $C_{12}H_{14}O_3$ | 69.88 | 69.88 | 6.84 | 7.16 |
| 6. Phenyl | $CH_2=CCH_3$ (with side chain) | $CH_3$ | M | 28 | 75(.05) | $C_{12}H_{14}O_3$ | 69.88 | 69.66 | 6.84 | 6.87 |
| 7. Phenyl | $CH_3CH_2CH=CH-$ | $CH_3$ | H | 86 | 160–164(15) | $C_{13}H_{16}O_3$ | 70.88 | 71.48 | 7.32 | 7.38 |
| 8. Cyclohexyl | $CH_3CH=CH-$ | $C_2H_5$ | H | 75 | 144–147(15) | $C_{13}H_{22}O_3$ | 68.99 | 69.33 | 9.80 | 9.77 |
| 9. Cyclohexyl | $CH_2=C-CH_3$ (with side chain) | $C_2H_5$ | M | 22 | 123–127(10) | $C_{13}H_{22}O_3$ | 68.99 | 68.72 | 9.80 | 9.92 |
| 10. Cyclohexyl | $CH_3CH_2CH=CH-$ | $C_2H_5$ | H | 100 | 80–82(.30) | $C_{14}H\geqq O_3$ | 69.96 | 70.04 | 10.07 | 10.21 |
| 11. Cyclohexyl | $(CH_3)2HCCH=CH-$ | $C_2H_5$ | H | 100 | 84–90(.08) | $C_{15}H_{26}O_3$ | 70.83 | 70.99 | 10.30 | 10.20 |

The final products of this invention, $R^1$, $R^2C(OH)COOR^3$, may be prepared from the lower alkyl substituted glycolates, $R^1$, $R^2C(OH)COOR^4$, by a number of general methods; these include the transesterification preparation of methyl esters in normal heptane (Method I), of ethyl esters in toluene (Method II) and of ethyl or methyl esters in benzene or ethyl esters in n-heptane (Method III). These general methods are as follows:

Methyl Esters in n-Heptane (Method I)

The ester (0.02–0.04 mole), the appropriate basic alcohol (0.025–0.06 mole), and a piece of sodium are suspended in 50 ml. of n-heptane in a flask equipped with a reflux head and a graduated receiver. The mixture is heated to 90°–100° (gentle reflux) and the methanol-heptane azeotrope collected periodically. Heating is continued until the theoretical amount of methanol is obtained or until no more methanol can be observed forming (usually 5–7 hours). The reaction mixture is allowed to cool, (generally overnight). In some cases the product precipitates and is filtered. The filtrate or the reaction mixture (in the cases when the product does not crystallize) is then washed with water and the organic layer is subsequently poured onto ice and conc. HCl (10 ml.) slurry. Ether is added and the layers separated. The water layer is then made strongly basic with a cold saturated sodium hydroxide solution and extracted with several portions of chloroform. The chloroform extracts are combined, dried and subsequently stripped in vacuo. The residue is then either distilled or recrystallized. If purification of the free base is difficult, the hydrochloride is prepared by standard techniques.

Ethyl Esters in Toluene (Method II)

The basic alcohol (0.03–0.04 mole), a piece of sodium (~0.05 g.), and 20 to 30 ml. of toluene are refluxed in a flask equipped with a small packed column and reflux head for about 0.25 to 2 hours until most of the sodium reacts. Then the ester (0.025 to 0.03 mole) dissolved in about 20–30 ml. of solvent is added dropwise (generally one to two hours) to the refluxing solution, and the resultant ethanol-toluene azeotrope is collected periodically. Reflux is continued for several hours. After the temperature is stabilized at 110°, 0.075 to 0.15 g. of NaOCH$_3$ is occasionally added. The reaction mixture is allowed to cool (generally overnight) and any solid that precipitates is filtered. The filtrate is then poured onto a slurry of ice and 10 ml. of conc. HCl. The layers are separated. The organic layer is washed several times with cold 6N HCl and the washings and original water layer are combined. The aqueous layer is cooled in an ice bath and made strongly basic with a cold saturated sodium hydroxide solution. The cold mixture is extracted quickly with several portions of chloroform. The chloroform extracts are dried and the volatile materials subsequently stripped in vacuo. The residue then is either distilled or recrystallized. In the cases where purification is difficult, the hydrochloride is prepared by dissolving the material in anhydrous ether and bubbling HCl into the solution. The hydrochloride is then recrystallized.

Ethyl or Methyl Esters in Benzene or Ethyl Esters in n-Heptane (Method III)

The ester (0.02 mole) and the appropriate basic alcohol (0.03 mole) and 50 ml. of solvent are placed in a 100 ml. flask equipped with a packed column and a reflux head. The solution is then refluxed for about 15 minutes to remove any traces of moisture present. A small piece of sodium is then added. The azeotrope is then collected periodically. More sodium is added occasionally and the reaction mixture is refluxed until no more azeotrope forms i.e., the boiling point of the solvent is attained and remains constant. The reaction time generally is 4 to 7 hours. The reaction mixture is then worked up as described above. This method, using benzene as solvent, is found to be the best—especially when quinuclidinol is used—and generally results in higher yields and cleaner products.

Specific examples follow; in each case the structure of the compound was confirmed by n.m.r. spectroscopy.

EXAMPLE 6

Preparation of 3-Quinuclidyl α-Phenyl-α-phenylethynylglycolate

A suspension of 3-quinuclidinol (5.1 g. 0.04 mole) and Na (~0.05 g.) in 20 ml. of toluene was heated to reflux in a flask equipped with a reflux head and stirrer. After the sodium reacted completely (about 15 minutes of refluxing), ethyl α-phenyl-α-phenylethynyl-glycolate (7.0 g., 0.025 mole) dissolved in 20 ml. of toluene was added very slowly over a two hour period. Towards the end of the addition a temperature drop of 6° was noted in the head and 10 ml. of the toluene-ethanol azeotrope slowly was distilled over. The reaction mixture was refluxed for an additional hour, and an additional 10 ml. of distillate was subsequently collected over a thirty minute period. The reaction mixture was poured on ice and acidified with 6N HCl. The toluene layer was separated and washed with several portions of 6N HCl. The combined water layers were neutralized with 10% NaOH, basified with potassium carbonate and extracted with chloroform several times. The chloroform layer was dried and subsequently stripped of volatile material in vacuo to leave a tacky solid. The material was washed with hot ether to give 5.2 g. (58%) of an off-white solid, m.p. 150°–90°. Recrystallization from benzene and then isopropanol yielded analytically pure material, m.p. 205°–8°.

Anal. Calcd. for $C_{23}H_{23}NO_3$: C, 76.43; H, 6.41; N, 3.88. Found: C, 76.69; H, 6.70; N, 3.96.

EXAMPLE 7

Preparation of 1-Methyl-3-piperidyl α-Phenyl-α-phenylethynyl-glycolate

Ethyl α-phenyl-α-phenylethynyl-glycolate (7.0 g., 0.025 mole), 1-methyl-3-piperidinol (4.6 g., 0.04 mole) and sodium (~0.05 g.) yielded (5.0 g., 58%) of the desired compound by the procedure described above. In this case, however, the crude product was precipitated from the reaction mixture by the addition of benzene and 20°–40° petroleum ether. Recrystallization from ether yielded the pure solid, m.p. 167.0–169.4°.

Anal. Calcd. for $C_{22}H_{23}NO_3$: C, 75.63; H, 6.63; N, 4.01. Found: C, 75.85; H, 6.74; N, 4.66.

EXAMPLE 8

Preparation of 1-Methyl-4-piperidyl α-Phenyl-α-phenylethynyl-glycolate

Ethyl α-phenyl-α-phenylethynyl-glycolate (7.0 g., 0.025 mole), 1-methyl-4-piperidinol (4.6 g., 0.04 mole) and sodium (~0.05 g.) yielded 6.4 g. (74%) of the desired compound by the previously described procedure. The pure material melted at 160.6°–161.4°, after recrystallization from benzene.

Anal. Calcd. for $C_{22}H_{23}NO_3$: C, 75.63; H, 6.63; N, 4.01. Found: C, 75.37; H, 6.40; N, 4.28.

EXAMPLE 9

Preparation of 3-Quinuclidyl α-Cyclohexyl-α-phenylethynyl-glycolate

3-Quinuclidinol (2.5 g., 0.020 mole) was dissolved in 50 ml. of toluene and a small piece of sodium (~0.05 g.) was added. The toluene was refluxed for about 40 minutes until all the sodium had reacted. Ethyl α-cyclohexyl-α-phenylethynylglycolate (4.3 g., 0.015 mole) was subsequently added as a solution in 35 ml. of toluene, over an hour period, to the refluxing reaction mixture. The reaction mixture was refluxed for an additional 20 hours. During the last four hours about 40 ml. of solvent was distilled over. The reaction mixture was then worked-up as described previously. The basic chloroform extract yielded 4.0 g. of an oil, which partially crystallized upon the addition of anhydrous ether. A total of 1.6 g. (27%) of crude product was obtained. Recrystallization from hexane gave analytically pure material, m.p. 171°-172°.

Anal. Calcd. for $C_{23}H_{29}NO_3$: C, 75.17; H, 7.96; N, 3.82. Found: C, 75.38; H, 8.05; N, 4.03.

EXAMPLE 10

Preparation of 1-Methyl-4-piperidyl α-Cyclohexyl-α-phenylethynyl-glycolate Hydrochloride This ester was prepared by a method similar to the ones described above from the reaction of ethyl α-cyclohexyl-α-phenylethynyl-glycolate (4.3 g., 0.015 mole), 1-methyl-4-piperidinol (2.3 g., 0.020 mole) and sodium (~0.05 g.) in toluene. The chloroform extract of the basic phase of the reaction mixture, when stripped of volatile components in vacuo, yielded an oil. The oil was dissolved in dry ether and treated with HCl (gas) to give an oily solid. Recrystallization from a chloroform-benzene mixture gave about 0.6 g. (10%) of the desired hydrochloride, m.p. about 198°-200°.

Anal. Calcd. for $C_{22}H_{30}NO_3Cl$: C, 67.42; H, 7.71; N, 3.57. Found: C, 66.44; H, 8.18; N, 4.57.

EXAMPLE 11

Preparation of 3-Quinuclidyl α-Cyclopentyl-α-phenylethynylglycolate

3-Quinuclidinol (3.8 g., 0.030 mole) and about 0.05 g. of sodium were refluxed in 50 ml. of toluene, in a flask equipped with a reflux head, until all the sodium reacted. Then, ethyl α-cyclopentyl-α-phenylethynyl-glycolate (5.4 g., 0.02 mole) in 35 ml. of solvent was added dropwise over an hour period. No temperature drop was noted in the reflux head. The reaction mixture was refluxed for about 18 hours and then about 40 ml. of solvent was distilled from the reaction flask over a four hour period. The reaction mixture was cooled, and dry 20°-40° petroleum ether was added. A tarry solid formed and was filtered. The solid was treated with hot hexane to yield 3.2 g. (45%) of crude product melting about 115° C. The pure compound, m.p. 137°-39°, was obtained by recrystallization from hexane.

Anal. Calcd. for $C_{22}H_{27}NO_3$: C, 74.75; H, 7.70; N, 3.97. Found: C, 74.30; H, 7.74; N, 4.45.

EXAMPLE 12

Preparation of 1-Methyl-4-piperidyl α-Cyclopentyl-α-phenylethynylglycolate

The reaction of ethyl α-cyclopentyl-α-phenylethynylglycolate (5.4 g., 0.02 mole), 1-methyl-4-piperidinol (3.5 g., 0.03 mole) and sodium (~0.05 g.) in about 85 ml. of toluene was carried out essentially as described in the preceding preparation. However, no solid precipitated upon the addition of 20°-40° petroleum ether at the end of the reflux period. The reaction mixture therefore was poured on ice and HCl and extracted with ether. The ether extracts were washed with dilute HCl. The washings and water layer were combined, made basic with sodium carbonate, and extracted with chloroform. Drying of the basic extract and subsequent distillation of the volatile compound in vacuo yielded a tarry residue which, when treated with ether and hexane gave 1.5 g. (22%) of crude product. The pure compound, m.p. 104°-105°, was obtained by recrystallization from hexane.

Anal. Calcd. for $C_{21}H_{27}NO_3$: C, 73.87; H, 7.97; N, 4.11. Found: C, 73.77; H, 7.95; N, 4.31.

EXAMPLE 13

Preparation of 1-Methyl-3-piperidyl α-Cyclopentyl-α-phenylethynyl-glycolate

Sodium (~0.05 g.) and 1-methyl-3-piperidinol (4.0 g., 0.035 mole) were refluxed in 250 ml. of dry n-heptane in a reaction flask equipped with a Dean-Stark trap until all of the sodium reacted. Then 6.5 g. (0.024 mole) of ethyl α-cyclopentyl-α-phenylethynylglycolate, undiluted, was added dropwise over a 0.25 hour period. The reaction mixture was subsequently refluxed for 20 hours, and about 30 ml. of solvent was collected toward the end of that period. The reaction mixture was kept overnight. No crystallization occurred during that time, but some tarry material was present and was filtered. Ether (acidic) and chloroform (basic) extracts were made of the filtrate as described previously. The chloroform extract yielded, after the solvent was stripped, 6.2 g. of a red-brown oil. The oil was dissolved in ether and petroleum ether (20°-40°) was added until turbidity was produced. The material was then placed in a freezer for four days and the product precipitated. It weighed 3.2 g., (39%) and melted at about 85° after being filtered and dried. The solid was recrystallized from 20°-40° petroleum ether. The first batch yielded off white crystals melting at 112°-113°.

Anal. Calcd. for $C_{21}H_{27}NO_3$: C, 73.87; H, 7.97; N, 4.11. Found: C, 73.43; H, 7.98; N, 4.88.

Concentration of the mother liquor led to the precipitation of white needles of m.p. 88°-96°.

Anal. Calcd. for $C_{21}H_{27}NO_3$: C, 73.87; H, 7.97; N, 4.11. Found: C, 74.06; H, 7.94; N, 4.22.

The infrared spectra of both solids were identical and confirmed the desired structure. The n.m.r. spectra also verified the structure. The only discernible difference in the two spectra was a slight shift to a lower field of the methylene hydrogens adjacent to the nitrogen in the lower melting material.

EXAMPLE 14

Preparation of 1-Methyl-4-piperidyl α-Ethynyl-α-phenyl-glycloate

1-Methyl-4-piperidinol (3.5 g. 0.03 mole) was refluxed for about 1.5 hours with sodium (~0.05 g.) in 150 ml. of heptane. Methyl α-ethynyl-α-phenyl-glycolate (4.2 g., 0.02 mole) was then added dropwise, intermittently over a one hour period. The reaction mixture was refluxed for an additional 0.5 hour. A total of 0.25 ml. of methanol was collected (theoretical=0.8 ml.). More solvent (50 ml.) was added as an equal amount was simultaneously distilled from the reaction flask. The reaction mixture was refluxed a total of five hours after the ester addition, but no more methanol was collected. The reaction mixture began to darken considerably, and heating was stopped. The mixture was left undisturbed overnight, during which time an oily solid precipitated. It was filtered, washed with water, and dried. The crude product weighed 3.4 g. (63%) and melted at 145°. An analytical sample melted at 148°-49.5° after recrystallization from hexane, benzene, and then hexane again.

Anal. Calcd. for $C_{16}H_{19}NO_3$: C, 70.31; H, 7.01; N, 5.12. Found: C, 70.49; H, 7.12; N, 5.21.

IR confirmed the structure of the product.

EXAMPLE 15

Preparation of 1-Methyl-3-piperidyl α-Ethynyl-α-phenylglycolate

1-Methyl-3-piperidinol (3.5 g., 0.03 mole) and a small piece of sodium (~0.05 g.) were refluxed in 150 ml. of n-heptane for about 1 hour in a flask equipped with a small distilling head. Methyl α-ethynyl-α-phenylglycolate (4.0 g., 0.02 mole) was then added intermittently over a one hour period with the temperature of the reaction mixture maintained at 90°. The reaction mixture was heated at 90°-95° for three hours during which time very little methanol was collected. The reaction mixture was subsequently refluxed for 11 hours and the azeotrope collected periodically. During this time sodium methoxide (0.075 g.) was added and 50 ml. of fresh n-heptane was added as an equal volume of distillate was collected simultaneously. These operations were carried out twice. Heating was stopped and a total of 0.3 ml. (38% of theory) of methanol was obtained. As the reaction mixture cooled, an oil settled out. The n-heptane was decanted and the residue was washed with ice water (3 × 10 ml.). Ether and ice were added to the oil and the mixture worked up as described in Example 12, to yield 1.9 g. (35%) of the product as a yellow oil. Crystallization was effected by dissolving the material in ether, adding 30°-60° petroleum ether to produce turbidity and refrigerating the solution for several days. The product melted at 92°-95° after recrystallization from hexane.

Anal. Calcd. for $C_{16}H_{19}NO_3$: C, 70.31; H, 7.01; N, 5.12. Found: C, 70.29; H, 6.72; N, 5.34.

Other examples of final products prepared by transesterification of lower alkyl glycolates are given in Tables 4 through 13. In each case, the assigned structure of the compound was in agreement with its n.m.r. spectrum.

TABLE 4

ACTYLENIC 1-METHYL-4-PIPERIDYL PHENYL-GLYCLOLATES, $R^1,R^2C(OH)COOR^3$[1]
$R^1$ = Phenyl, $R^3$ = 1-methyl-4-piperidyl (4P)

| $R^2$ | Empirical Formula | Crude Yield % | M.P. °C. | C Calcd. | C Found | H Calcd. | H Found | N Calcd. | N Found |
|---|---|---|---|---|---|---|---|---|---|
| 1. $CH_3C\equiv C-$ | $C_{17}H_{21}NO_3$ | 90 | 172-172.5 | 71.06 | 70.74 | 7.37 | 7.17 | 4.87 | 4.95 |
| 2. $HC\equiv C-CH_2-$ | $C_{17}H_{21}NO_3$ | 67 | 135-137[2] (0.005) | 71.06 | 71.21 | 7.37 | 7.67 | 4.87 | 5.12 |
| 3. $CH_3CH_2C\equiv C-$ | $C_{18}H_{23}NO_3$ | 95 | 119-121 | 71.73 | 71.58 | 7.69 | 7.46 | 4.65 | 4.94 |
| 4. $CH_2=C(CH_3)C\equiv C-$ | $C_{19}H_{23}NO_3$ | 72 | 130-131 | 72.81 | 72.76 | 7.40 | 7.73 | 4.47 | 4.72 |
| 5. $CH_3(CH_2)_2C\equiv C-$ | $C_{19}H_{25}NO_3$ | 92 | 111-114 | 72.35 | 72.53 | 7.99 | 8.13 | 4.44 | 4.75 |
| 6. $(CH_3)_2CHC\equiv C-$ | $C_{19}H_{25}NO_3$ | 97 | 120-121 | 72.35 | 72.50 | 7.99 | 7.94 | 4.44 | 4.70 |
| 7. $CH_3(CH_2)_3C\equiv C-$ | $C_{20}H_{27}NO_3$ | 98 | 90-90.5 | 72.92 | 73.05 | 8.26 | 8.39 | 4.25 | 4.54 |
| 8. $(CH_3)_3CC\equiv C-$ | $C_{20}H_{27}No_3$ | 91 | 153-155 | 72.92 | 73.20 | 8.26 | 8.44 | 4.25 | 4.34 |
| 9. $CH_3(CH_2)_4C\equiv C-$ | $C_{21}H_{29}NO_3$ | 90 | 83-84 | 73.44 | 73.59 | 8.51 | 8.65 | 4.08 | 4.38 |

[1] Prepared by Method I
[2] B.P., °C. (mm.)

TABLE 5

ACETYLENIC 3-QUINUCLIDYL PHENYL-GLYCOLATE ESTERS[1], $R^1$, $R^2C(OH)COOR^3$
$R^1$ = Phenyl, $R^3$ = 3-Quinuclidyl (3Q)

| $R^2$ | Empirical Formula | Crude Yield % | M.P., °C. | C Calcd. | C Found | H Calcd. | H Found | N Calcd. | N Found |
|---|---|---|---|---|---|---|---|---|---|
| 1. $CH_3C\equiv C-$ | $C_{18}H_{21}NO_3$[2] | 62 | 193-196[4] 139-142 | 72.22 | 71.85 72.47 | 7.07 | 7.15 6.96 | 4.68 | 4.88 4.83 |
| 2. $HC\equiv C-CH_2-$ | $C_{18}H_{21}NO_3$ | 78 | 158-164[3] (.002) | 71.73 | 71.55 | 7.69 | 7.93 | 4.65 | 4.95 |
| 3. $CH_3CH_2C\equiv C-$ | $C_{19}H_{23}NO_3$ | 35 | 111.5-115.5[4] 175-178 | 72.81 | 73.05 72.81 | 7.40 | 7.68 7.55 | 4.47 | 4.59 4.77 |
| 4. $CH_2=C(CH_3)C\equiv C-$ | $C_{20}H_{23}NO_3$[2] | 71 | 160.5-161.5[4] 115-121 | 73.82 | 73.57 74.15 | 7.12 | 7.20 7.37 | 4.30 | 4.77 4.29 |
| 5. $CH_3(CH_2)_2C\equiv C-$ | $C_{20}H_{25}NO_3$ | 77 | 85-100[4] 145-146 | 73.36 | 73.37 73.09 | 7.70 | 7.94 7.94 | 4.28 | 5.40 4.55 |
| 6. $(CH_3)_2CHC\equiv C-$ | $C_{20}H_{25}NO_3$ | 37 | 165-167.5 | 73.36 | 73.16 | 7.70 | 7.51 | 4.28 | 4.28 |
| 7. $CH_3(CH_2)_3C\equiv C-$ | $C_{21}H_{27}NO_3$ | 80 | 101-123 | 73.86 | 73.84 | 7.97 | 7.98 | 4.11 | 4.29 |
| 8. $(CH_3)_3CC\equiv C-$ | $C_{21}H_{27}NO_3$ | 88 | 184-186[4] 137-142 | 73.86 | 73.74 74.14 | 7.97 | 8.01 7.84 | 4.11 | 4.13 3.98 |
| 9. $CH_3(CH_2)_4C\equiv C-$ | $C_{22}H_{29}NO_3$ | 86 | 126-127 | 74.33 | 74.26 | 8.22 | 8.23 | 3.95 | 3.99 |

[1] Prepared by transesterification Method III except where noted.
[2] Prepared by transesterification Method I.
[3] B.P., °C. (mm.).
[4] Two isomers isolated

TABLE 6

ACETYLENIC 1-METHYL-4-PIPERIDYL ALKYL- and CYCLOALATES-GLYCOLATES[1], $R^1$, $R^2C(OH)COOR^3$,
$R^3$ = 1-METHYL-4-PIPERIDYL (4P)

| $R^1$ | $R^2$ | Empirical Formula | Crude Yield % | M.P. °C. or B.P. °C.(mm) | C Calcd. | C Found | H Calcd. | H Found | O Calcd. | O Found |
|---|---|---|---|---|---|---|---|---|---|---|
| 1. Isopropyl | $CH_3C\equiv C-$ | $C_{14}H_{23}NO_3$ | 94 | 81-82 | 66.37 | 66.52 | 9.15 | 9.26 | 5.53 | 5.83 |

TABLE 6-continued

ACETYLENIC 1-METHYL-4-PIPERIDYL ALKYL- and CYCLOALATES-GLYCOLATES[1], $R^1$, $R^2C(OH)COOR^3$, $R^3$ = 1-METHYL-4-PIPERIDYL (4P)

| | | | | | Analysis | | | | | |
|---|---|---|---|---|---|---|---|---|---|---|
| | | | | | C | | H | | O | |
| $R^1$ | $R^2$ | Empirical Formula | Crude Yield % | M.P. °C. or B.P. °C.(mm) | Calcd. | Found | Calcd. | Found | Calcd. | Found |
| 2. Cylopropyl | $CH_3C\equiv C-$ | $C_{14}H_{21}NO_3$ | 66 | 108–110(.001) | 66.90 | 66.91 | 8.42 | 8.73 | 5.57 | 5.69 |
| 3. Cyclopentyl | $CH_3C\equiv C-$ | $C_{16}H_{25}NO_3$ | 72 | 123–124.5 | 68.79 | 68.95 | 9.02 | 8.85 | 5.01 | 5.15 |
| 4. Cyclopentyl | $CH_3CH_2C\equiv C-$ | $C_{17}H_{27}NO_3$ | 100 | 91–93 | 69.59 | 69.57 | 9.28 | 9.23 | 4.77 | 4.88 |
| 5. Cyclopentyl | $CH_2=C(CH_3)C\equiv C-$ | $C_{18}H_{27}NO_3$ | 67 | 76–78 | 70.79 | 70.78 | 8.91 | 9.04 | 4.59 | 4.65 |
| 6. Cyclopentyl | $(CH_3)_2CHC\equiv C-$ | $C_{18}H_{29}NO_3$ | 98 | 123–127(.0005) | 70.32 | 70.48 | 9.51 | 9.55 | 4.56 | 4.79 |
| 7. Cyclohexyl | $CH_3C\equiv C-$ | $C_{17}H_{27}NO_3$ | 75 | 125–126.5 | 69.59 | 69.87 | 9.28 | 9.20 | 4.77 | 4.85 |
| 8. Cyclohexyl | $CH_3CH_2C\equiv C-$ | $C_{18}H_{29}NO_3$ | 34 | 106–107 | 70.32 | 70.44 | 9.51 | 9.66 | 4.56 | 4.86 |
| 9. Cyclohexyl | $CH_2=C(CH_3)C\equiv C-$ | $C_{19}H_{29}NO_3$ | 80 | 146–150(.001) | 71.44 | 71.50 | 9.15 | 9.41 | 4.39 | 4.50 |
| 10. Cyclohexyl | $(CH_3)_2CHC\equiv C-$ | $C_{19}H_{31}NO_3$ | 98 | 93–95 | 70.99 | 71.22 | 9.72 | 9.50 | 4.36 | 4.35 |
| 11. Cyclopentyl | $HC\equiv C-$ | $C_{15}H_{23}NO_3$ | 57 | 108–109 | 67.89 | 67.97 | 8.74 | 8.92 | 5.28 | 5.47 |

[1]Prepared by transesterification method 1.

TABLE 7

ACETYLENIC 3-QUINUCLIDYL ALKYL- AND CYLOALKYL-GLYCOLATES[1], $R^1R^2C(OH)COOR^3$, $R^3$ = 3-quinuclidyl (3Q)

| | | | | | Analysis | | | | | |
|---|---|---|---|---|---|---|---|---|---|---|
| | | | | | C | | H | | N | |
| $R^1$ | $R^2$ | Empirical Formula | Crude Yield % | M.P. °C. | Calcd. | Found | Calcd. | Found | Calcd. | Found |
| 1. Isopropyl | $CH_3C\equiv C-$ | $C_{15}H_{25}NO_3$ | 83 | 175–178[2] | 67.89 | 67.71 | 8.74 | 8.69 | 5.28 | 5.56 |
| | | | | 114–117 | | 67.97 | | 8.78 | | 5.06 |
| 2. Cyclopropyl | $CH_3C\equiv C-$ | $C_{15}H_{21}NO_3$ | 27 | 166–168 (d) | 68.41 | 68.16 | 8.04 | 7.99 | 5.32 | 5.57 |
| 3. Cyclopentyl | $HC\equiv C-$ | $C_{16}H_{23}NO_3$ | 67 | 103–38 | 69.28 | 68.41 | 8.36 | 8.81 | 5.05 | 6.05 |
| 4. Cyclopentyl | $CH_3C\equiv C-$ | $C_{17}H_{25}NO_3$ | 93 | 152–153.5[2] | 70.07 | 69.77 | 8.65 | 8.77 | 4.81 | 4.66 |
| | | | | 93–98 | | 69.95 | | 8.97 | | 4.59 |
| 5. Cyclopentyl | $CH_3CH_2C\equiv C-$ | $C_{18}H_{27}NO_3$ | 66 | 143–145[2] | 70.79 | 70.56 | 8.91 | 8.79 | 4.59 | 4.80 |
| | | | | 83–90 | | 70.50 | | 9.02 | | 4.85 |
| 6. Cyclopentyl | $CH_2=C(CH_3)C\equiv C-$ | $C_{19}H_{27}NO_3$ | 75 | 121.5–126.5 | 71.89 | 71.88 | 8.57 | 8.39 | 4.41 | 4.58 |
| 7. Cyclopentyl | $(CH_3)_2CHC\equiv C-$ | $C_{19}H_{29}NO_3$ | 83 | 90–110 | 71.44 | 71.34 | 9.15 | 9.44 | 4.39 | 4.44 |
| 8. Cyclohexyl | $CH_3C\equiv C-$ | $C_{18}H_{27}NO_3$ | 52 | 111.5–115.5 | 72.81 | 73.05 | 7.40 | 7.68 | 4.47 | 4.59 |
| 9. Cyclohexyl | $CH_3CH_2C\equiv C-$ | $C_{19}H_{29}NO_3$ | 77 | 134–137[2] | 71.44 | 71.36 | 9.15 | 8.95 | 4.39 | 4.52 |
| | | | | 175–176.5 | | 71.59 | | 9.07 | | 4.36 |
| 10. Cyclohexyl | $CH_2=C(CH_3)C\equiv C-$ | $C_{20}H_{29}NO_3$ | 82 | 171–172[2] | 72.47 | 72.52 | 8.82 | 8.93 | 4.28 | 4.48 |
| | | | | 149–160 | | 72.53 | | 8.85 | | 4.46 |
| 11. Cyclohexyl | $(CH_3)_2CH=C-$ | $C_{20}H_{31}NO_3$ | 94 | 135–158 | 72.03 | 71.73 | 9.37 | 9.10 | 4.20 | 4.58 |

[1]Prepared by Method III.
[2]Two isomers isolated.

TABLE 8

MISCELLANEOUS ACETYLENIC BASIC GLYCOLATES $R^1$, $R^2C(OH)COOR^3$ [1]

| | | | | | | Analysis | | | | | |
|---|---|---|---|---|---|---|---|---|---|---|---|
| | | | | | | C | | H | | N | |
| $R^1$ | $R^2$ | $R^3$ | Empirical Formula | Crude Yield % | M.P., °C. or B.P., °C. (mm.) | Calcd. | Found | Calcd. | Found | Calcd. | Found |
| 1. Cyclopentyl | $CH_3C\equiv C-$ | 2M3Q[2] | $C_{18}H_{27}NO_3$ | 100 | 150–155(.005) | 70.79 | 70.82 | 8.91 | 8.95 | 4.59 | 4.52 |
| 2. Cyclopentyl | $CH_3C\equiv C-$ | 3α-T[3] | $C_{18}H_{27}NO_3$ | 100 | 153–158(.007) | 70.79 | 70.82 | 8.91 | 8.92 | 4.59 | 4.59 |
| 3. Phenyl | $CH_3C\equiv C-$ | 3Py[4] | $C_{16}H_{19}NO_3$ | 62 | 93–98[10] | 70.31 | 70.54 | 7.01 | 7.21 | 5.13 | 5.31 |
| | | | | | 98–111 | | 70.44 | | 6.80 | | 4.94 |
| 4. Phenyl | $CH_3C\equiv C-$ | 3P[5] | $C_{17}H_{21}NO_3$ | 81 | 115–150 | 71.06 | 71.41 | 7.37 | 7.31 | 4.87 | 5.17 |
| 5. Phenyl | $CH_3C\equiv C-$ | 2PCH$_2$[6] | $C_{18}H_{23}NO_3$ | 100 | 160–165(.003) | 71.73 | 71.87 | 7.69 | 7.77 | 4.65 | 4.72 |
| 6. Phenyl | $CH_3C\equiv C-$ | 4PCH$_2$[7] | $C_{18}H_{24}NO_3Cl$[8] | 84 | 184–185 | 63.99 | 64.01 | 7.16 | 7.19 | 4.15 | 4.39 |
| 7. Phenyl | $CH_3C\equiv C-$ | 3 α-T[3] | $C_{19}H_{23}NO_3$ | 87 | 178(.001) | 72.81 | 73.09 | 7.40 | 7.51 | 4.47 | 4.57 |
| 8. Phenyl | $CH_3CH_2C\equiv C-$ | 2M3Q[2] | $C_{20}H_{25}NO_3$ | 100 | 175–181(.003) | 73.36 | 73.11 | 7.70 | 7.79 | 4.28 | 4.46 |
| 9. Phenyl | $CH_3CH_2C\equiv C-$ | 3 α-T[3] | $C_{20}H_{25}NO_3$ | 100 | 180–190(.002) | 73.36 | 73.07 | 7.70 | 7.64 | 4.28 | 4.52 |
| 10. Cyclohexyl | $CH_3C\equiv C-$ | GMAP[9] | $C_{16}H_{27}NO_3$ | 84 | 119–125(.007) | 68.29 | 68.04 | 9.67 | 9.80 | 4.88 | 5.14 |

[1]Prepared by method III except where otherwise noted.
[2]2-Methyl-3-quinuclidyl.
[3]3α-Tropanyl.
[4]1-Methyl-3-pyrrolidinyl.
[5]1-Methyl-3-piperidyl prepared by method I.
[6]1-Methyl-3-piperidylmethyl.
[7]1-Methyl-4-piperidylmethyl.
[8]Hydrochloride salt.
[9]γ-Dimethylaminopropyl.
[10]Two isomers isolated.

TABLE 9

OLEFINIC 1-METHYL-4-PIPERIDYL PHENYLGLYCOLATES
$R^1, R^2C(OH)COOR^3$, $R^1$ = phenyl, $R^3$ = 1-methyl-4-piperidyl(4P)

| | | | | Analyses | | | | | |
|---|---|---|---|---|---|---|---|---|---|
| | Empirical | Crude | M.P., °C./B.P., | C | | H | | N | |
| $R^2$ | Formula | Yield % | °C.(mm.) | Calcd. | Found | Calcd. | Found | Calcd. | Found |
| 1. $CH_3CH=CH(c)$[1] | $C_{17}H_{23}NO_3$[2] | 83 | 130–143(.002) | 70.56 | 70.43 | 8.01 | 8.20 | 4.84 | 5.12 |
| 2. $CH_3CH=CH(t)$[3] | $C_{17}H_{23}NO_3$[4] | 83 | 124–128(.0005) | 70.56 | 70.24 | 8.01 | 8.08 | 4.84 | 4.80 |
| 3. $CH_3\underset{|}{C}=CH_2$ | $C_{17}H_{23}NO_3$[2] | 81 | 130–134(.008) | 70.56 | 70.38 | 8.01 | 8.11 | 4.84 | 4.66 |
| 4. $CH_3CH_2CH=CH-$ | $C_{18}H_{25}NO_3$[2] | 85 | 84–95 | 71.25 | 71.16 | 8.31 | 8.37 | 4.62 | 4.51 |
| 5. $CH_3(CH_2)_3CH=CH-$ | $C_{20}H_{29}NO_3$[4] | 67 | 145–150(.001) | 72.47 | 72.19 | 8.82 | 8.84 | 4.23 | 4.27 |
| 6. $C_6H_5CH=CH-$ | $C_{22}H_{25}NO_3$[5] | 90 | 99.5–101 | 75.18 | 75.01 | 7.17 | 7.29 | 3.99 | 4.33 |

[1]cis isomer.
[2]Prepared by method I.
[3]trans isomer.
[4]Prepared by method III.
[5]Prepared by method II.

TABLE 10

OLEFINIC 3-QUINUCLIDYL PHENYLGLYCOLATES
$R^1, R^2C(OH)COOR^3$, $R^1$ = phenyl, $R^3$ = 3-quinuclidyl(3Q)

| | | | | Analyses | | | | | |
|---|---|---|---|---|---|---|---|---|---|
| | Empirical | Crude | M.P. °C. or | C | | H | | N | |
| $R^2$ | Formula | Yield % | B.P., °C. (mm) | Calcd. | Found | Calcd. | Found | Calcd. | Found |
| 1. $CH_3CH=CH(c)$[1] | $C_{18}H_{23}NO_3$[2] | 85 | 152–155(.002) | 71.73 | 71.55 | 7.69 | 7.93 | 4.65 | 4.95 |
| 2. $CH_3CH=CH(t)$[3] | $C_{18}H_{23}NO_3$[2] | 80 | 174–176(.0005) | 71.73 | 71.53 | 7.69 | 7.67 | 4.65 | 4.58 |
| 3. $CH_3-\underset{|}{C}=CH_2$ | $C_{18}H_{23}NO_3$[2] | 90 | 88–117 | 71.73 | 71.68 | 7.69 | 7.41 | 4.65 | 4.70 |
| 4. $CH_3CH_2CH=CH-$ | $C_{19}H_{25}NO_3$[2] | 92 | 93–113 137–138 | 72.35 | 72.40 72.14 | 7.99 | 7.89 7.88 | 4.44 | 4.61 4.72 |
| 5. $CH_3(CH_2)_3CH=CH-$ | $C_{21}H_{29}NO_3$[2] | 65 | 162–163(.001) | 73.43 | 72.94 | 8.51 | 8.64 | 4.08 | 3.97 |
| 6. $C_6H_5CH=CH-$ | $C_{23}H_{25}NO_3$[4] | 82 | 124–140 | 75.79 | 75.62 | 7.19 | 6.85 | 3.85 | 4.06 |

[1]cis isomer.
[2]Prepared by method III.
[3]trans isomer.
[4]Prepared by method II.

TABLE 11

OLEFINIC 1-METHYL-4-PIPERIDYL ALKYL- AND CYCLOALKYL-GLYCOLATES[1]
$R^1, R^2C(OH)COOR^3$, $R^3$ = 1-methyl-4-piperidyl(4P)

| | | | | | Analyses | | | | | |
|---|---|---|---|---|---|---|---|---|---|---|
| | | Empirical | Crude | B.P., | C | | H | | N | |
| $R^1$ | $R^2$ | Formula | Yield % | °C. (mm) | Calcd. | Found | Calcd. | Found | Calcd. | Found |
| 1. Isopropyl | $CH_3CH=CH-$ | $C_{14}H_{25}NO_3$ | 74 | 94–98(.004) | 65.85 | 65.78 | 9.87 | 9.97 | 5.49 | 5.79 |
| 2. Cyclopentyl | $CH_3CH=CH-$ | $C_{16}H_{27}NO_3$ | 90 | 124–125(.001) | 68.29 | 68.30 | 9.67 | 9.78 | 4.98 | 4.88 |
| 3. Cyclopentyl | $CH_3CH_2CH=CH-$ | $C_{17}H_{29}NO_3$ | 93 | 118–120(.001) | 69.11 | 69.33 | 9.90 | 10.12 | 4.74 | 4.64 |
| 4. Cyclopentyl | $(CH_3)_2CHCH=CH-$ | $C_{18}H_{31}NO_3$ | 55 | 122–123(.003) | 69.86 | 69.87 | 10.10 | 10.06 | 4.53 | 4.61 |
| 5. Cyclohexyl | $CH_3CH=CH-$ | $C_{17}H_{29}NO_3$ | 97 | 121–124(.008) | 69.11 | 69.21 | 9.90 | 10.14 | 4.74 | 4.83 |
| 6. Cyclohexyl | $CH_3CH_2CH=CH-$ | $C_{18}H_{31}NO_3$ | 68 | 127(.002) | 69.86 | 69.62 | 10.10 | 10.14 | 4.53 | 4.42 |
| 7. Cyclohexyl | $(CH_3)_2CHCH=CH-$ | $C_{19}H_3NO_3$ | 39 | 126–128(.001) | 70.55 | 70.83 | 10.28 | 10.17 | 4.33 | 4.02 |

[1]Prepared by method III.

TABLE 12

OLEFINIC 3-QUINUCLIDYL ALKYL—AND CYCLOALKYL—GLYCOLATES[1]
$R^1, R^2C(OH)COOR^3$, $R^3$ = 3—quinuclidyl(3Q)

| | | | | | Analyses | | | | | |
|---|---|---|---|---|---|---|---|---|---|---|
| | | Empirical | Crude | B.P., | C | | H | | N | |
| $R^1$ | $R^2$ | Formula | Yield % | °C. (mm) | Calcd. | Found | Calcd. | Found | Calcd. | Found |
| 1. Isopropyl | $CH_3CH=CH-$ | $C_{15}H_{25}NO_3$ | 100 | 105–108(.002) | 67.38 | 67.33 | 9.43 | 9.52 | 5.24 | 5.31 |
| 2. Cyclopentyl | $CH_3CH=CH-$ | $C_{17}H_{27}NO_3$ | 92 | 140–142(.001) | 69.59 | 69.86 | 9.28 | 9.22 | 4.77 | 4.65 |
| 3. Cyclopentyl | $CH_3CH_2CH=CH-$ | $C_{18}H_{29}NO_3$ | 99 | 136–140(.001) | 70.32 | 70.03 | 9.51 | 9.40 | 4.56 | 4.84 |
| 4. Cyclopentyl | $(CH_3)_2CHCH=CH-$ | $C_{19}H_{31}NO_3$ | 60 | 131–137(.002) | 70.99 | 70.72 | 9.72 | 9.72 | 4.36 | 4.57 |
| 5. Cyclohexyl | $CH_3CH=CH-$ | $C_{18}H_{29}NO_3$ | 72 | 143–149(.001) | 70.32 | 70.03 | 9.51 | 9.68 | 4.56 | 4.46 |
| 6. Cyclohexyl | $CH_3CH_2CH=CH-$ | $C_{19}H_{31}NO_3$ | 76 | 140–142(.002) | 70.99 | 70.95 | 9.72 | 9.53 | 4.36 | 4.66 |
| 7. Cyclohexyl | $(CH_3)_2CHCH=CH-$ | $C_{20}H_{33}NO_3$ | 39 | 137–140(.002) | 71.60 | 71.47 | 9.42 | 9.75 | 4.18 | 4.46 |

[1]Prepared by method III.

TABLE 13
MISCELLANEOUS OLEFINIC BASIC GLYCOLATES [1]
$R^1,R^2C(OH)COOR^3$

| | | | Empirical | Crude Yield | B.P. °C. (mm) | C | | H | | N | |
|---|---|---|---|---|---|---|---|---|---|---|---|
| $R^1$ | $R^2$ | $R^3$ | Formula | % | or M.P. °C. | Calcd. | Found | Calcd. | Found | Calcd. | Found |
| 1. Cyclopentyl | $CH_3CH=CH-$ | $2M3Q^2$ | $C_{18}H_{29}NO_3$ | 63 | 128–130(.006) | 70.32 | 70.53 | 9.51 | 9.50 | 4.56 | 4.83 |
| 2. Cyclopentyl | $(CH_3)_2CHCH=CH-$ | $2M3Q^2$ | $C_{20}H_{33}NO_3$ | 26 | 126–127(.001) | 71.60 | 71.61 | 9.92 | 10.17 | 4.18 | 4.48 |
| 3. Cyclohexyl | $(CH_3)_2CHCH=CH-$ | $BAE^3$ | $C_{17}H_{29}NO_3$ | 74 | 108–111(.001) | 69.11 | 69.43 | 9.90 | 9.95 | 4.74 | 4.36 |
| 4. Phenyl | $C_6H_5CH=CH-$ | $3P^4$ | $C_{44}H_{26}NO_3Cl^5$ | 56 | 207–209 | 68.13 | 68.23 | 6.75 | 6.63 | 3.61 | 3.69 |

[1] Prepared by method III except where noted.
[2] 2—Methyl—3—quinuclidyl.
[3] Beta(1—aziridinyl)ethyl.
[4] 1—Methyl—3—piperidyl — method II used.
[5] Hydrochloride salt.

The alternate method of preparing an ester of a substituted glyoxylic acid and a tertiary amino nitrogen-containing alcohol, $R^1COCOOR^3$, and subsequent alkylation to a final product $R^1$, $R^2C(OH)COOR^3$, is as follows:

EXAMPLE 16

Preparation of 3-Quinuclidyl α-Ethynyl-α-phenylglycolate

The intermediate 3-quinuclidyl phenylglyoxylate was prepared by the general method described for transesterification of substituted ethyl glycolates (Method II). The work-up procedure was modified slightly in that the reaction mixture was cooled and then washed with several portions of ice water to remove the unreacted quinuclidinol. The organic layer was subsequently dried and stripped of volatile components in vacuo. The residue was then distilled to give the product. Thus, ethyl phenylglyoxylate (17.8 g., 0.1 mole), 3-quinuclidinol (14.0 g., 0.1 mole) and sodium (0.05 g.) in 100 ml. of toluene yielded 13.4 g. (52%) of 3-quinuclidyl phenylglyoxylate, b.p. 136°–41° (0.005 mm.). An analytical sample distilled at 146°–47° (0.005 mm.).

Anal. Calcd. for $C_{15}H_{17}NO_3$: C, 69.48; H, 6.61; N, 5.40. Found: C, 69.47; H, 6.88; N, 5.49.

The above ester (13.0 g., 0.5 mole) was dissolved in 500 ml. of THF, cooled to 5° in an ice bath and treated, dropwise with a THF solution of ethynylmagnesium bromide prepared by known procedures from magnesium (1.3 g., 0.055 g. atom), ethyl bromide (5.5 g., 0.05 mole) and excess acetylene. The reaction mixture was stirred at room temperature for 23 hours, and then poured onto 100 ml. of cold water containing 20 g. of ammonium chloride. The mixture was extracted with ether and then with chloroform. The organic extracts were combined, dried and subsequently stripped of volatile components in vacuo to yield 12.0 g. of oil. The product (3.6 g., 25%) was precipitated from the oil by the addition of ether, and melted at 154°–156° C. after recrystallization from hexane. N.m.r. spectroscopy verified the structural assignments.

Anal. Calcd. for $C_{17}H_{19}NO_3$: C, 71.56; H, 6.71; N, 4.91. Found: C, 71.46; H, 6.90; N, 5.00.

The products of this invention showed mydriatic activity at very low doses (low $ED_{50}$mg./kg.) as measured in the mouse by intravenous injection, and were relatively non-toxic (high $LD_{50}$, mg./kg.), indicating high therapeutic ratios. The time of mydriasis of representative compounds also was measured. A 0.001% solution was placed in the eye of a rat and the onset time, that time necessary to reach complete mydriasis, 4 mm. dilation, and the duration of mydriasis, that time necessary for the eyes to return to normal, were recorded. These data are set forth in Tables 14, 15, 16 and 17. The benzilate is included as the first compound in Table 14 for reference.

TABLE 14

| | | | Mouse | | Mydriasis Time Rat (Mins.) | |
|---|---|---|---|---|---|---|
| $R^1$ | $R^2$ | $R^3$ | $ED_{50}$ | $LD_{50}$ | Onset | Duration |
| +Phenyl | +Phenyl | 3Q | .02 | 20 | 15* | >380* |
| Phenyl | HC≡C— | 4P | .04 | 63 | | |
| Phenyl | HC≡C— | 3P | ~10 | >100 | | |
| Phenyl | HC≡C— | 3Q | .32 | >100 | | |
| Phenyl | $CH_3C≡C-$ | 3PY(A) | .18 | 100 | 25* | 53* |
| Phenyl | $CH_3C≡C-$ | 3PY(B) | .03 | 80 | 4* | 10* |
| Phenyl | $CH_3C≡C-$ | 3P | .56 | 56 | | |
| Phenyl | $CH_3C≡C-$ | 4P | .02 | 56 | 5 | 84 |
| Phenyl | $CH_3C≡C-$ | 3P—$CH_2$— | .02 | 63 | | |
| Phenyl | $CH_3C≡C-$ | 4P—$CH_2$— | .18 | 56 | 5* | 30* |
| Phenyl | $CH_3C≡C-$ | 3Q(A) | .02 | 45 | 8 | 120 |
| Phenyl | $CH_3C≡C-$ | 3Q(B) | .01 | 50 | 20 | 140 |
| Phenyl | $CH_3C≡C-$ | 3αT | .01 | 79 | 24 | 119 |
| Phenyl | HC≡C—$CH_2$— | 4P | .10 | 63 | 4* | 30* |
| Phenyl | HC≡C—$CH_2$— | 3Q | .06 | 31 | 9* | 29* |
| Phenyl | $CH_3CH_2C≡C-$ | 4P | .007 | 36 | 9,6 | 55,62 |
| Phenyl | $CH_3CH_2C≡C-$ | 3Q(A) | .02 | 40 | 19,16 | 120,144 |
| Phenyl | $CH_3CH_2C≡C-$ | 3Q(B) | .04 | 28 | | |
| Phenyl | $(CH_3)_2CHC≡C-$ | 4P | .02 | 22 | 15 | 70 |
| Phenyl | $(CH_3)_2CHC≡C-$ | 3Q | .06 | 36 | | |
| Phenyl | $(CH_3)_3CC≡C-$ | 4P | .06 | 18 | | |
| Phenyl | $(CH_3)_3CC≡C-$ | 3Q(A) | .10 | 32 | | |

TABLE 14-continued

| R¹ | R² | R³ | Mouse ED$_{50}$ | Mouse LD$_{50}$ | Mydriasis Time Rat (Mins.) Onset | Mydriasis Time Rat (Mins.) Duration |
|---|---|---|---|---|---|---|
| Phenyl | (CH$_3$)$_3$CC≡C— | 3Q(B) | .10 | 32 | | |
| Phenyl | CH$_3$(CH$_2$)$_2$C≡C— | 4P | .08 | 22 | | |
| Phenyl | CH$_3$(CH$_2$)$_2$C≡C— | 3Q | .10 | 35 | | |
| Phenyl | CH$_3$(CH$_2$)$_3$C≡C— | 3Q | .08 | 25 | | |
| Phenyl | CH$_3$(CH$_2$)$_3$C≡C— | 4P | .02 | 20 | | |
| Phenyl | CH$_3$(CH$_2$)$_3$C≡C— | 3Q | .18 | 20 | | |
| Phenyl | CH$_3$(CH$_2$)$_4$C≡C— | 4P | .18 | 16 | | |
| Phenyl | CH$_3$(CH$_2$)$_4$C≡C— | 3Q(A) | >10 | >100 | | |
| Phenyl | CH$_3$(CH$_2$)$_4$C≡C— | 3Q(B) | .02 | 16 | | |
| Phenyl | CH$_2$=C(CH$_3$)C≡C— | 4P | .03 | 25 | 16 | 119 |
| Phenyl | CH$_2$=C(CH$_3$)C≡C— | 3Q(A) | .20 | 14 | | |
| Phenyl | CH$_2$=C(CH$_3$)C≡C— | 3Q(B) | .10 | 26 | | |
| Phenyl | C$_6$H$_5$C≡C— | 3P | 10 | >100 | | |
| Phenyl | C$_6$H$_5$C≡C— | 4P | .32 | 41 | | |
| Phenyl | C$_6$H$_5$C≡C— | 3Q | 1 | 32 | | |

+Prior Art Compound
*Partial Mydriasis

TABLE 15

| R¹ | R² | R³ | Mouse ED$_{50}$ | Mouse LD$_{50}$ | Mydriasis Time Rat, (Mins.) Onset | Mydriasis Time Rat, (Mins.) Duration |
|---|---|---|---|---|---|---|
| Isopropyl | CH$_3$C≡C— | 4P | .06 | 79 | | |
| Isopropyl | CH$_3$C≡C— | 3Q(A) | .02 | 112 | | |
| Isopropyl | CH$_3$C≡C— | 3Q(B) | .32 | 63 | | |
| Cyclopropyl | CH$_3$C≡C— | 4P | .18 | 45 | | |
| Cyclopropyl | CH$_3$C≡C— | 3Q | .08 | 79 | | |
| Cyclopentyl | HC≡C— | 4P | .03 | 79 | 15 | 30 |
| Cyclopentyl | HC≡C— | 3Q | .02 | 50 | | |
| Cyclopentyl | CH$_3$C≡C— | 4P | .03 | 50 | 3 | 101 |
| Cyclopentyl | CH$_3$C≡C— | 3Q(A) | .003 | 79 | 10 | 223 |
| Cyclopentyl | CH$_3$C≡C— | 3Q(B) | .08 | 79 | | |
| Cyclopentyl | CH$_3$CH$_2$C≡C— | 4P | .02 | 56 | | |
| Cyclopentyl | CH$_3$CH$_2$C≡C— | 3Q(A) | .02 | 56 | | |
| Cyclopentyl | CH$_3$CH$_2$C≡C— | 3Q(B) | .08 | 50 | | |
| Cyclopentyl | CH$_2$=C(CH$_3$)C≡C— | 4P | .06 | 56 | 15 | 55 |
| Cyclopentyl | CH$_2$=C(CH$_3$)C≡C— | 3Q | .06 | 45 | | |
| Cyclopentyl | (CH$_3$)$_2$CHC≡C— | 4P | .03 | 63 | | |
| Cyclopentyl | (CH$_3$)$_2$CHC≡C— | 3Q | .06 | 36 | | |
| Cyclopentyl | C$_6$H$_5$C≡C— | 3P(A) | 10 | >100 | | |
| Cyclopentyl | C$_6$H$_5$C≡C— | 4P | 10 | | | |
| Cyclopentyl | C$_6$H$_5$C≡C— | 3Q | 10 | | | |
| Cyclohexyl | CH$_3$C≡C— | 4P | .02 | 45 | 4 | 99 |
| Cyclohexyl | CH$_3$C≡C— | 3Q(A) | .04 | 71 | 10* | 45* |
| Cyclohexyl | CH$_3$C≡C— | 3Q(B) | .02 | 63 | | |
| Cyclohexyl | CH$_3$CH$_2$C≡C— | 4P | .06 | 45 | 20 | 150 |
| Cyclohexyl | CH$_3$CH$_2$C≡C— | 3Q(A) | .02 | 50 | 10 | 270 |
| Cyclohexyl | CH$_3$CH$_2$C≡C— | 3Q(B) | .06 | 50 | | |
| Cyclohexyl | CH$_2$=C(CH$_3$)C≡C— | 4P | .05 | 40 | | |
| Cyclohexyl | CH$_2$=C(CH$_3$)C≡C— | 3Q(A) | .60 | 40 | 16 | 73 |
| Cyclohexyl | CH$_2$=C(CH$_3$)C≡C— | 3Q(B) | .20 | 40 | | |
| Cyclohexyl | (CH$_3$)$_2$CH—C≡C— | 4P | .08 | 56 | | |
| Cyclohexyl | (CH$_3$)$_2$CH—C≡C— | 3Q | .20 | 36 | | |
| Cyclohexyl | C$_6$H$_5$C≡C— | 4P | .32 | 121 | | |
| Cyclohexyl | C$_6$H$_5$C≡C— | 3Q | 10 | >100 | | |

*Partial Mydriasis

TABLE 16

| R¹ | R² | R³ | Mouse ED$_{50}$ | Mouse LD$_{50}$ | Mydriasis Time Rat (Mins.) Onset | Mydriasis Time Rat (Mins.) Duration |
|---|---|---|---|---|---|---|
| Phenyl | CH$_3$CH=CH— (C)+ | 4P | .01 | 32 | 6 | 71 |
| Phenyl | CH$_3$CH=CH— (C)+ | 3Q | .008 | 56 | 30* | 120* |
| Phenyl | CH$_3$CH=CH— (t)** | 4P | .02 | 45 | | |
| Phenyl | CH$_3$CH=CH— (t)** | 3Q | .02 | 45 | | |
| Phenyl | CH$_3$—C(|)=CH$_2$ | 4P | .03 | 36 | 25 | 105 |
| Phenyl | CH$_3$—C(|)=CH$_2$ | 3Q | .02 | 71 | 20 | 190 |
| Phenyl | C$_2$H$_5$CH=CH— | 4P | .05 | 40 | | |
| Phenyl | C$_2$H$_5$CH=CH— | 3Q(A) | .06 | 45 | | |
| Phenyl | C$_2$H$_5$CH=CH— | 3Q(B) | .06 | 40 | | |

*Partial Mydriasis
**trans-isomer
+cis-isomer

TABLE 17

| R¹ | R² | R³ | Mouse ED$_{50}$ | Mouse LD$_{50}$ | Mydriasis Time Rat (Mins.) Onset | Mydriasis Time Rat (Mins.) Duration |
|---|---|---|---|---|---|---|
| Isopropyl | CH$_3$CH=CH— | 4P | .30 | 63 | | |
| Isopropyl | CH$_3$CH=CH— | 3Q | .10 | 71 | | |
| Cyclopentyl | CH$_3$CH=CH— | 4P | .08 | 71 | 20 | 95 |
| Cyclopentyl | CH$_3$CH=CH— | 3Q | .03 | 71 | 5 | 375 |
| Cyclopentyl | CH$_3$CH=CH— | 2M3Q | .02 | 28 | | |
| Cyclopentyl | CH$_3$CH$_2$CH=CH— | 4P | .06 | 71 | 15 | 90 |
| Cyclopentyl | CH$_3$CH$_2$CH=CH— | 3Q | .02 | 56 | 15 | 150 |
| Cyclopentyl | (CH$_3$)$_2$CHCH=CH— | 4P | .20 | 36 | | |
| Cyclopentyl | (CH$_3$)$_2$CHCH=CH— | 3Q | .03 | 40 | | |
| Cyclohexyl | CH$_3$CH=CH— | 4P | .02 | 112 | 10* | 25* |
| Cyclohexyl | CH$_3$CH=CH— | 3Q | .03 | 100 | 15 | 140 |
| Cyclohexyl | CH$_3$CH$_2$CH=CH— | 3Q | .23 | >100 | 10 | 170 |
| Cyclohexyl | (CH$_3$)$_2$CHCH=CH— | 4P | .06 | 40 | | |
| Cyclohexyl | (CH$_3$)$_2$CHCH=CH— | 3Q | .20 | 45 | | |

*Partial Mydriasis

The time course effects as measured on the basis of the time course of mydriasis correlate directly with the time course effects of other anticholinergic actions such as cycloplegia, effects on mental and neurological diseases, and effects on the gastrointestinal tract.

What is claimed is:

1. A substituted glycolic acid having the generic formula:

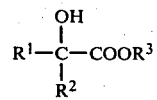

in which R¹ is a carbocyclic or branched aliphatic group of 3 to 8 carbon atoms, R² is a branched or linear aliphatic group containing 3 to 10 carbon atoms with 1 to 2 olefinic or acetylenic bonds and R³ is an alkyl or cyclic group of 4 to 12 carbon atoms containing a tertiary amino nitrogen.

2. A composition according to claim 1 in which R³ is a cyclic group of 4 to 10 carbon atoms containing a tertiary amino nitrogen.

3. A composition according to claim 1 in the form of an acid addition salt thereof.

4. The composition of claim 1 in the form of a quaternary ammonium salt thereof.

UNITED STATES PATENT AND TRADEMARK OFFICE
CERTIFICATE OF CORRECTION

PATENT NO. : 4,465,834
DATED : August 14, 1984
INVENTOR(S) : Burton M. Baum and Hugo Stange It is certified that error appears in the above—identified patent and that said Letters Patent is hereby corrected as shown below:

Column 3, Table 1, under $R_2$, "4 $CH_3(CH_{21})_2C\equiv C-$" should read --4 $CH_3(CH_2)_2C\equiv C-$ --; Table 2, under $R_2$, "5. $CH_2\equiv C(CH_3)C\equiv C-$" should read --5. $CH_2=C(CH_3)C\equiv C-$ --. Column 6, line 12, "weighting" should read --weighing--; line 47, under Empirical Formula, "10. $C_{14}H=O_3$" should read --10. $C_{14}H_{24}O_3$--. Column 10, line 50, "-glycloate" should read -- -glycolate--. Column 11, Table 4, Heading, "ACTYLENIC" should read --ACETYLENIC--; Table 5, under heading $R_2$, "4. $CH_2\equiv C(CH_3)C\equiv C-$" should read --4. $CH_2=C(CH_3)C\equiv C-$ --. Column 12, Table 4, heading "PHENYL-GLYCLOLATES," should read --PHENYL-GLYCO-LATES,--; Table 6, heading "CYCLOALATES-GLYCOLATES" should read --CYCLOALKYL-GLYCOLATES--. Column 13, Table

UNITED STATES PATENT AND TRADEMARK OFFICE
CERTIFICATE OF CORRECTION

PATENT NO. : 4,465,834

DATED : August 14, 1984

INVENTOR(S) : Burton M. Baum and Hugo Stange

It is certified that error appears in the above—identified patent and that said Letters Patent is hereby corrected as shown below:

6-continued, under $R_2$, "5. $CH_2\equiv C(CH_3)C\equiv C-$" should read --5. $CH_2=C(CH_3)C\equiv C-$ --, Table 6-continued under $R_2$, "9. $CH_2\equiv C(CH_3)C\equiv C-$" should read --9. $CH_2=C(CH_3)C\equiv C-$ --; Table 7, under $R_2$, "6. $CH_2\equiv C(CH_3)C\equiv C-$" should read --6. $CH_2=C(CH_3)C\equiv C-$ --; Table 7, under $R_2$, "10. $CH_2\equiv C(CH_3)C\equiv C-$" should read --10. $CH_2=C(CH_3)C\equiv C-$ --; Table 8, under $R^3$, "$2PCH_2^6$" should read --$3PCH_2^6$ --. Columns 13-14, Table 6, heading "CYCLOALATES-GLYCOLATES" should read --CYCLOALKYL-GLYCOLATES--. Column 17, Table 13, under Empirical Formula, "4. $C_{44}H_{26}NO_3Cl^5$" should read --4. $C_{22}H_{26}NO_3Cl^5$--. Column 19, Table 14-continued, under $R^2$, "$CH_3(CH_2)_3C\equiv C-$" should read --$CH_3(CH_2)_2C\equiv C-$ --.

Signed and Sealed this

Sixteenth Day of April 1985

[SEAL]

Attest:

DONALD J. QUIGG

Attesting Officer     Acting Commissioner of Patents and Trademarks